(12) United States Patent
Boesen

(10) Patent No.: US 12,087,415 B2
(45) Date of Patent: *Sep. 10, 2024

(54) SYSTEM AND METHOD FOR POPULATING ELECTRONIC MEDICAL RECORDS WITH WIRELESS EARPIECES

(71) Applicant: BRAGI GmbH, Munich (DE)

(72) Inventor: Peter Vincent Boesen, Munich (DE)

(73) Assignee: BRAGI GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/348,886

(22) Filed: Jul. 7, 2023

(65) Prior Publication Data

US 2023/0352131 A1 Nov. 2, 2023

Related U.S. Application Data

(63) Continuation of application No. 17/843,461, filed on Jun. 17, 2022, now Pat. No. 11,710,545, which is a (Continued)

(51) Int. Cl.
G16H 10/65 (2018.01)
A61B 5/00 (2006.01)
(Continued)

(52) U.S. Cl.
CPC .......... *G16H 10/65* (2018.01); *A61B 5/0008* (2013.01); *A61B 5/002* (2013.01); *A61B 5/0022* (2013.01);
(Continued)

(58) Field of Classification Search
CPC ........ G16H 10/65; G16H 15/00; G16H 40/67; G16H 80/00; A61B 5/0008; A61B 5/002;
(Continued)

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Edwards, Wireless Sensors Relay Medical Insight to Patients and Caregivers, May 2012, IEEE Signal Processing Magazine [8], doi: 10.1109/MSP.2012.2183489 (Year: 2012).*
(Continued)

*Primary Examiner* — Joy Chng
(74) *Attorney, Agent, or Firm* — Goodhue, Coleman & Owens, P.C.

(57) ABSTRACT

A system, method and wireless earpieces for populating an electronic medical record utilizing wireless earpieces. The sensor measurements are analyzed. The sensor measurements are associated with the electronic medical record of the user. The electronic medical record of the user is populated with the sensor measurements. Communications including the electronic medical record are communicated.

20 Claims, 8 Drawing Sheets

Related U.S. Application Data continuation of application No. 15/927,865, filed on Mar. 21, 2018, now Pat. No. 11,380,430.

(60) Provisional application No. 62/475,063, filed on Mar. 22, 2017.

(51) Int. Cl.
*A61B 5/0205* (2006.01)
*G16H 15/00* (2018.01)
*G16H 40/67* (2018.01)
*G16H 80/00* (2018.01)
*H04R 1/10* (2006.01)

(52) U.S. Cl.
CPC ........ *A61B 5/02055* (2013.01); *A61B 5/6817* (2013.01); *G16H 15/00* (2018.01); *G16H 40/67* (2018.01); *H04R 1/1016* (2013.01); *G16H 80/00* (2018.01); *H04R 2420/07* (2013.01)

(58) Field of Classification Search
CPC . A61B 5/0022; A61B 5/02055; A61B 5/6817; H04R 1/1016; H04R 2420/07
USPC .......................................................... 705/2–3
See application file for complete search history.

(56) References Cited

U.S. PATENT DOCUMENTS

| | | | |
|---|---|---|---|
| 3,047,089 A | 7/1962 | Zwislocki |
| D208,784 S | 10/1967 | Sanzone |
| 3,586,794 A | 6/1971 | Michaelis |
| 3,696,377 A | 10/1972 | Wall |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| 5,444,786 A | 8/1995 | Raviv |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| 5,844,996 A | 12/1998 | Enzmann et al. |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,185,152 B1 | 2/2001 | Shen |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,563,301 B2 | 5/2003 | Gventer |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| 7,532,901 B1 | 5/2009 | LaFranchise et al. |
| D601,134 S | 9/2009 | Elabidi et al. |
| 7,825,626 B2 | 11/2010 | Kozisek |
| 7,859,469 B1 | 12/2010 | Rosener et al. |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |
| 8,679,012 B1 | 3/2014 | Kayyali |
| 8,719,877 B2 | 5/2014 | VonDoenhoff et al. |
| 8,774,434 B2 | 7/2014 | Zhao et al. |

(56) References Cited

U.S. PATENT DOCUMENTS

| | | |
|---|---|---|
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong |
| D777,710 S | 1/2017 | Palmborg |
| 9,544,689 B2 | 1/2017 | Fisher et al. |
| D788,079 S | 5/2017 | Son et al. |
| 9,711,062 B2 | 7/2017 | Ellis et al. |
| 9,729,979 B2 | 8/2017 | Özden |
| 9,767,709 B2 | 9/2017 | Ellis |
| 9,848,257 B2 | 12/2017 | Ambrose et al. |
| 11,380,430 B2 | 7/2022 | Boesen |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251423 A1* | 11/2005 | Bellam .................. G16H 10/60 705/3 |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0269785 A1 | 11/2007 | Yamanoi |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf |
| 2008/0146892 A1* | 6/2008 | LeBoeuf .................. A61B 5/4812 600/300 |
| 2008/0187163 A1 | 8/2008 | Goldstein |
| 2008/0215239 A1 | 9/2008 | Lee |
| 2008/0253583 A1 | 10/2008 | Goldstein |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0226017 A1 | 9/2009 | Abolfathi et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0303073 A1 | 12/2009 | Gilling et al. |
| 2009/0304210 A1 | 12/2009 | Weisman |
| 2010/0033313 A1 | 2/2010 | Keady et al. |
| 2010/0166206 A1 | 7/2010 | Macours |
| 2010/0203831 A1 | 8/2010 | Muth |
| 2010/0210212 A1 | 8/2010 | Sato |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0103609 A1 | 5/2011 | Pelland et al. |
| 2011/0137141 A1 | 6/2011 | Razoumov |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2011/0293105 A1 | 12/2011 | Arie et al. |
| 2012/0057740 A1 | 3/2012 | Rosal |
| 2012/0155670 A1 | 6/2012 | Rutschman |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0204617 A1 | 8/2013 | Kuo et al. |
| 2013/0293494 A1 | 11/2013 | Reshef |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0188516 A1* | 7/2014 | Kamen .................. G16H 40/60 705/3 |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0275928 A1* | 9/2014 | Acquista ............... A61N 1/3987 600/382 |
| 2014/0276227 A1 | 9/2014 | Pérez |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0148989 A1 | 5/2015 | Cooper et al. |
| 2015/0149207 A1* | 5/2015 | O'Keefe ............... G06Q 10/109 705/3 |
| 2015/0181356 A1 | 6/2015 | Krystek et al. |

(56) References Cited

U.S. PATENT DOCUMENTS

| | | |
|---|---|---|
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree |
| 2015/0373467 A1 | 12/2015 | Gelter |
| 2015/0373474 A1 | 12/2015 | Kraft et al. |
| 2016/0033280 A1 | 2/2016 | Moore |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0100262 A1 | 4/2016 | Inagaki |
| 2016/0116351 A1* | 4/2016 | Gross ............... A61B 5/0022 702/131 |
| 2016/0119737 A1 | 4/2016 | Mehnert et al. |
| 2016/0124707 A1 | 5/2016 | Ermilov |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0210429 A1* | 7/2016 | Ortiz ...................... H04L 63/10 |
| 2016/0253994 A1 | 9/2016 | Panchapagesan et al. |
| 2016/0324478 A1 | 11/2016 | Goldstein |
| 2016/0353196 A1 | 12/2016 | Baker et al. |
| 2016/0360350 A1 | 12/2016 | Watson et al. |
| 2017/0021257 A1 | 1/2017 | Gilbert |
| 2017/0046503 A1 | 2/2017 | Cho |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0185716 A1* | 6/2017 | Rodriguez .............. G06F 16/70 |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |
| 2018/0103874 A1* | 4/2018 | Lee ..................... A61B 5/4833 |

FOREIGN PATENT DOCUMENTS

| | | | |
|---|---|---|---|
| CN | 104837094 A | 8/2015 | |
| EP | 1469659 A1 | 10/2004 | |
| EP | 1017252 A3 | 5/2006 | |
| EP | 2903186 A1 | 8/2015 | |
| GB | 2074817 | 11/1981 | |
| GB | 2508226 A | 5/2014 | |
| JP | 06292195 | 10/1998 | |
| WO | 2008103925 A1 | 8/2008 | |
| WO | 2008113053 A1 | 9/2008 | |
| WO | 2007034371 A3 | 11/2008 | |
| WO | 2011001433 A2 | 1/2011 | |
| WO | 2012071127 A1 | 5/2012 | |
| WO | 2013134956 A1 | 9/2013 | |
| WO | WO-2013177357 A1 * | 11/2013 | ........... A61B 5/0022 |
| WO | 2014043179 A2 | 3/2014 | |
| WO | 2014046602 A1 | 3/2014 | |
| WO | 2014043179 A3 | 7/2014 | |
| WO | 2015061633 A2 | 4/2015 | |
| WO | 2015110577 A1 | 7/2015 | |
| WO | 2015110587 A1 | 7/2015 | |
| WO | 2016032990 A1 | 3/2016 | |
| WO | 2016187869 A1 | 12/2016 | |
| WO | WO-2017062621 A1 * | 4/2017 | ........... A61B 5/0022 |

OTHER PUBLICATIONS

A. H. M. Akkermans, T. A. M. Kevenaar and D. W. E. Schobben, "Acoustic ear recognition for person identification," Published In:

(56) References Cited

OTHER PUBLICATIONS

Fourth IEEE Workshop on Automatic Identification Advanced Technologies (AutoID'05), Buffalo, NY, USA, 2005, pp. 219-223.
Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XPO55334602, DOI: 10.3390/s151025681 the whole document.
Announcing the $3,333,333 Stretch Goal (Feb. 24, 2014) pp. 1-14.
Ben Coxworth: "Graphene-based ink could enable low-cost, foldable electronics", "Journal of Physical Chemistry Letters", Northwestern University, (May 22, 2013), pp. 1-7.
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is On Facebook (2014), pp. 1-51.
Bragi Update—Arrival of Prototype Chassis Parts—More People—Awesomeness (May 13, 2014), pp. 1-8.
Bragi Update—Chinese New Year, Design Verification, Charging Case, More People, Timeline(Mar. 6, 2015), pp. 1-18.
Bragi Update—First Sleeves From Prototype Tool—Software Development Kit (Jun. 5, 2014), pp. 1-8.
Bragi Update—Let's Get Ready to Rumble, A Lot to Be Done Over Christmas (Dec. 22, 2014), pp. 1-18.
Bragi Update—Memories From April—Update on Progress (Sep. 16, 2014), pp. 1-15.
Bragi Update—Memories from May—Update on Progress—Sweet (Oct. 13, 2014), pp. 1-16.
Bragi Update—Memories From One Month Before Kickstarter—Update on Progress (Jul. 10, 2014), pp. 1-17.
Bragi Update—Memories From The First Month of Kickstarter—Update on Progress (Aug. 1, 2014), pp. 1-16.
Bragi Update—Memories From The Second Month of Kickstarter—Update on Progress (Aug. 22, 2014), pp. 1-15.
Bragi Update—New People @Bragi—Prototypes (Jun. 26, 2014), pp. 1-9.
Bragi Update—Office Tour, Tour to China, Tour to CES (Dec. 11, 2014), pp. 1-14.
Bragi Update—Status on Wireless, Bits and Pieces, Testing-Oh Yeah, Timeline(Apr. 24, 2015), pp. 1-18.
Bragi Update—The App Preview, The Charger, The SDK, Bragi Funding and Chinese New Year (Feb. 11, 2015), pp. 1-19.
Bragi Update—What We Did Over Christmas, Las Vegas & CES (Jan. 19, 2014), pp. 1-21.
Bragi Update—What We Did Over Christmas, Las Vegas &CES (Jan. 19, 2015), pp. 1-21.
Bragi Update—Years of Development, Moments of Utter Joy and Finishing What We Started(Jun. 5, 2015), pp. 1-21.
Bragi Update—Alpha 5 and Back to China, Backer Day, On Track(May 16, 2015), pp. 1-15.
Bragi Update—Beta2 Production and Factory Line(Aug. 20, 2015), pp. 1-16.
Bragi Update—Certifications, Production, Ramping Up (Nov. 13, 2015), pp. 1-15.
Bragi Update—Developer Units Shipping and Status(Oct. 5, 2015), pp. 1-20.
Bragi Update—Developer Units Started Shipping and Status (Oct. 19, 2015), pp. 1-20.
Bragi Update—Developer Units, Investment, Story and Status(Nov. 2, 2015), pp. 1-14.
Bragi Update—Getting Close(Aug. 6, 2015), pp. 1-20.
Bragi Update—On Track, Design Verification, How It Works and What's Next(Jul. 15, 2015), pp. 1-17.
Bragi Update—On Track, On Track and Gems Overview (Jun. 24, 15), pp. 1-19.
Bragi Update—On Track, On Track and Gems Overview (Jun. 24, 2015), pp. 1-19.
Bragi Update—Status on Wireless, Supply, Timeline and Open House@Bragi(Apr. 1, 2015), pp. 1-17.
Bragi Update—Unpacking Video, Reviews on Audio Perform and Boy Are We Getting Close(Sep. 10, 2015), pp. 1-15.
Healthcare Risk Management Review, "Nuance updates computer-assisted physician documentation solution" (Oct. 20, 2016), pp. 1-2.
Hoffman, "How to Use Android Beam to Wirelessly Transfer Content Between Devices", (Feb. 22, 2013).
Hoyt et al., "Lessons Learned from Implementation of Voice Recognition for Documentation in the Military Electronic Health Record System", The American Health Information Management Association (2017), pp. 1-8.
Hyundai Motor America, "Hyundai Motor Company Introduces A Health + Mobility Concept for Wellness in Mobility", Fountain Valley, Californa (2017), pp. 1-3.
International Search Report & Written Opinion, PCT/EP2016/070216 (Oct. 18, 2016) 13 pages.
International Search Report & Written Opinion, PCT/EP2016/070231 (Nov. 18, 2016) 12 pages.
International Search Report & Written Opinion, PCT/EP2016/070245 (Nov. 16, 2016) 10 pages.
International Search Report & Written Opinion, PCT/EP2016/070247 (Nov. 18, 2016) 13 pages.
International Search Report and Written Opinion, PCT/EP2016/070228 (Jan. 9, 2017) 13 pages.
Jain A et al: "Score normalization in multimodal biometric systems", Pattern Recognition, Elsevier, GB, vol. 38, No. 12, Dec. 31, 2005, pp. 2270-2285, XPO27610849, ISSN: 0031-3203.
Last Push Before the Kickstarter Campaign Ends on Monday 4pm CET (Mar. 28, 2014), pp. 1-7.
Nemanja Paunovic et al., "A methodology for testing complex professional electronic systems", Serbian Journal of Electrical Engineering, vol. 9, No. 1, Feb. 1, 2012, pp. 71-80, XPO55317584, Yu.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014), pp. 1-14.
Stretchgoal—The Carrying Case for The Dash (Feb. 12, 2014), pp. 1-9.
Stretchgoal—Windows Phone Support (Feb. 17, 2014), pp. 1-17.
The Dash + The Charging Case & The Bragi News (Feb. 21, 2014), pp. 1-12.
The Dash—A Word From Our Software, Mechanical and Acoustics Team + An Update (Mar. 11, 2014), pp. 1-7.
Update From Bragi—$3,000,000—Yipee (Mar. 22, 2014), pp. 1-11.
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

SYSTEM AND METHOD FOR POPULATING ELECTRONIC MEDICAL RECORDS WITH WIRELESS EARPIECES

PRIORITY STATEMENT

This application is a continuation of U.S. Non-Provisional application Ser. No. 17/843,461, filed on Jun. 17, 2022 which is a continuation of U.S. Non-Provisional application Ser. No. 15/927,865, filed on Mar. 21, 2018 now U.S. Pat. No. 11,380,430 which claims priority to Provisional Application No. 62/475,063 which are hereby incorporated by reference in their entireties.

FIELD OF THE INVENTION

The present invention relates to wireless earpieces. More specifically, but not exclusively, the present invention relates to populating electronic medical records utilizing biometric readings and other information from wireless earpieces.

BACKGROUND

One recognized use of wearable devices such as wireless earpieces is to provide biometric monitoring of a user in one form of another. However, the collection of such data by a set of wireless earpieces or other wearable devices may have limited utility. Such data may, in some cases, not be stored. Or if such data is stored, it may be stored only in a data silo. That is to say the data store for such data may be isolated and segregated from other data. In addition, such data may not always be accurate and complete.

Such data, however, may be rich in context and highly informative to health care providers who are involved with diagnosing and/or treating individuals. What is a needed is a better way to use biometric data from wireless earpieces or other wearable devices in a medical context.

SUMMARY

Therefore, it is a primary object, feature, or advantage of the present invention to improve over the state of the art.

It is a further object, feature, or advantage of the present invention to provide an earpiece which can monitor the biometric levels of the user.

It is a still further object, feature, or advantage of the present invention to provide an earpiece that can generate a medical and communicate the medical record to a health care provider.

Another object, feature, or advantage is to provide an efficient way for a medical professional or health care provider to monitor the status, condition, and biometrics of the user.

Yet another object, feature, or advantage is populating electronic medical records utilizing sensor readings from the wireless earpieces.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

The present invention provides a system, method, and wireless earpieces for populating an electronic medical record utilizing wireless earpieces. The sensor measurements are analyzed. The sensor measurements are associated with the electronic medical record of the user. Communications including the electronic medical record and sensor measurements are communicated directly to a medical professional. The medical professional validates the sensor measurements and the EMR.

According to one aspect a wireless earpiece is provided. The wireless earpiece may include a frame for fitting in an ear of a user. The wireless earpiece may also include a logic engine controlling functionality of the wireless earpiece. The wireless earpiece may include a plurality of sensors including at least one biometric sensor and at least one inertial sensor to perform sensor measurements of the user. The wireless earpiece also may include a transceiver communicating with at least a wireless device. The logic engine analyzes the sensor measurements, associates the sensor measurements with the EMR of the user, populates the EMR of the user with the sensor measurements, and sends communications including the EMR to at least an authorized medical professional for validation of the EMR.

According to another aspect, a wireless earpiece may contain a plurality of sensors, including at least one biometric sensor and at least one inertial sensor, that perform sensor measurements of a user utilizing the wireless earpiece. The wireless earpiece may also include a memory for storing sensor measurements. The wireless earpiece may include a processor for controlling the functionality of the wireless earpiece. The processor performs sensor measurement of a user utilizing sensors of the wireless earpiece, analyzes the sensor measurements, communicates the sensor measurements to a wireless device associated with a medical professional for validating and associating the sensor measurements with an electronic medical record of the user.

According to another aspect, a method for populating an electronic medical record (EMR) utilizing wireless earpieces is provided. The method includes linking the wireless earpieces to a wireless device, wherein the wireless earpieces include at least one earpiece further including: a frame, at least one microphone, a processor operatively connected to the at least one microphone, a wireless transceiver for connecting to the wireless device, the wireless transceiver operatively connected to the processor, at least one biometric sensor operatively connected to the processor, and at least one inertial sensor operatively connected to the processor. The method further includes performing sensor measurements of a user utilizing the at least one biometric sensor and the at least one inertial sensor of the wireless earpieces, populating the EMR of the user with the sensor measurements, the populating performed by the processor, sending communications including the EMR with the sensor measurements from the wireless earpieces to the wireless device, and receiving validation of the sensor measurements of the EMR from the health care provider and storing a record of the validation within the EMR. The method may further include generating the EMR of the user at the wireless earpieces. The method may further include populating the EMR with patient identifying information, the populating the EMR with patient identifying information performed by the processor of the wireless earpieces. The sensor measurements may include biometric readings of the user including at least pulse, blood pressure, audio, temperature, and user experienced forces.

According to another aspect, a wireless earpiece includes a frame for fitting in an ear of a user, a processor controlling functionality of the wireless earpiece, a plurality of sensors including at least one biometric sensor and at least one inertial sensor to perform sensor measurements of the user, and a transceiver communicating with at least a wireless device. The processor analyzes the sensor measurements, associates the sensor measurements with the EMR of the user, populates the EMR of the user with the sensor measurements, and electronically sends communications including the EMR to an electronic device associated with an authorized medical professional for validation of the EMR. The transceiver may establish a Bluetooth link with the wireless device, and the EMR may be saved in the wireless device. The EMR may be populated in response to the sensor measurements exceeding a threshold associated with the user. The sensor measurements may include biometric readings of the user include at least pulse, blood pressure, audio, blood oxygenation, temperature, and user experienced forces. The wireless earpiece may further include a memory in communication with the processor, wherein the memory stores the sensor measurements within the EMR for subsequent validation by the authorized medical professional. The EMR record may be further populated with identifying information of the patient and identifying information for the wireless earpieces.

According to another aspect, a wireless earpiece includes a plurality of sensors, including at least one biometric sensor and at least one inertial sensor, that perform sensor measurements of a user utilizing the wireless earpiece. The wireless earpiece may further include a memory for storing sensor measurements, and a processor for controlling the functionality of the wireless earpiece. The processor performs or controls sensor measurement of a user utilizing sensors of the wireless earpiece, analyzes the sensor measurements, communicates the sensor measurements to a wireless device associated with a medical professional for validating and associating the sensor measurements with an electronic medical record of the user. The sensor measurements may be analyzed to prepare the sensor measurements for communication to the wireless device. The wireless earpiece may provide for updating the EMR utilizing the sensor measurements.

DETAILED DESCRIPTION

Figure 1:
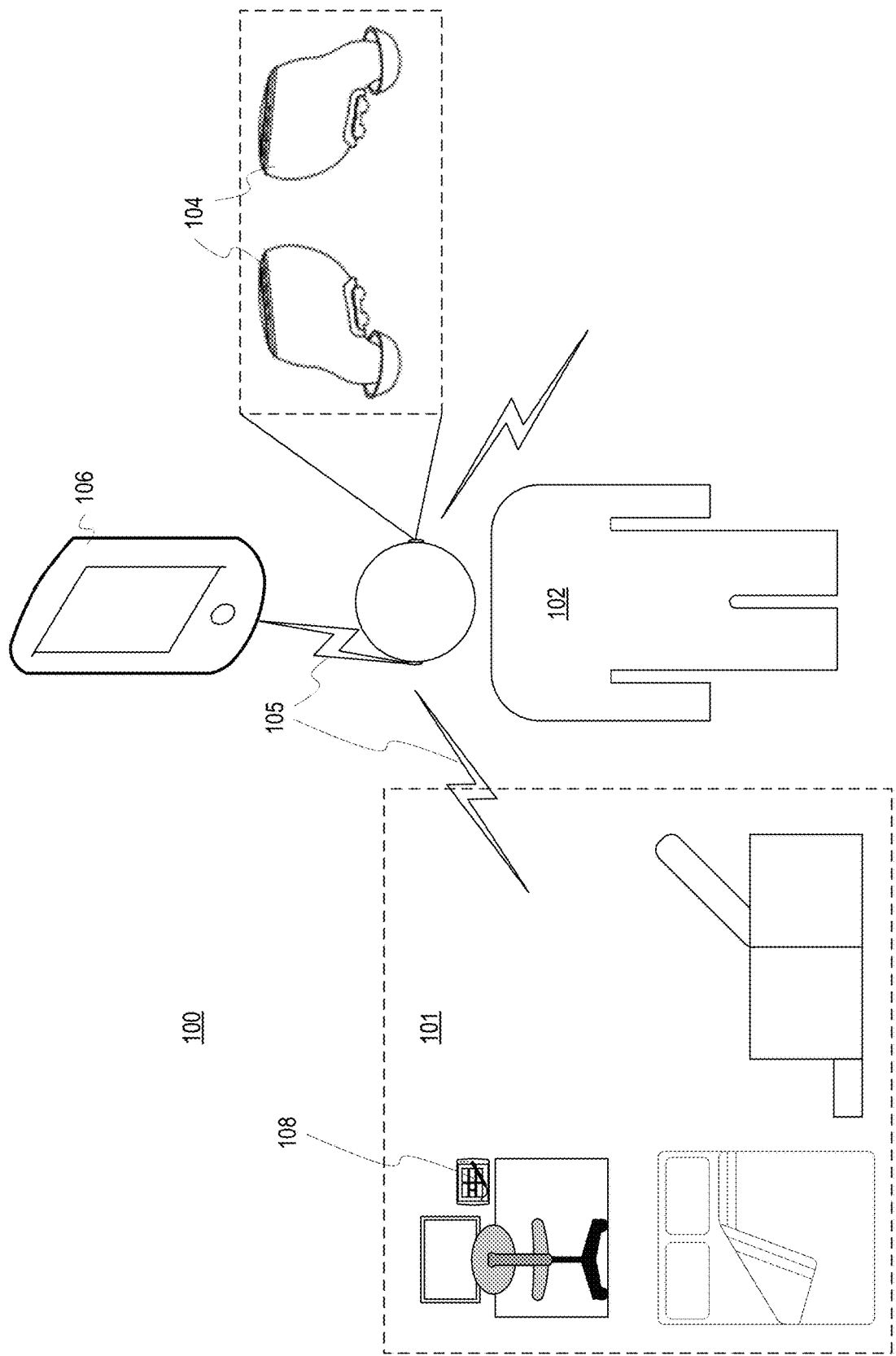
FIG. 1 is a pictorial representation of a communication system.

The invention is not to be limited to the particular embodiments described herein. In particular, the invention contemplates numerous variations in populating electronic medical records (EMRs) using wearable devices. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

The illustrative embodiments provide a system, method, and wireless devices for populating EMRs. The EMRs may be populated utilizing information and biometrics, inertial data, biological data, physiological data, or environmental data measured by the wireless earpieces. The EMRs may be stored locally by the wireless earpieces or the associated biometric, inertial, physiological, biological or environmental information may be communicated to one or more additional wireless earpieces, computing, communications, or medical devices.

The wireless earpieces may be part of a personal area network. The wireless earpieces may be utilized to control, communicate, manage, or interact with a number of other wearable devices, such as smart glasses, helmets, smart glass, watches or wrist bands, chest straps, implants, displays, clothing, or so forth. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols, standards, or signals, such as INSTEON, IrDA, Wireless USB, Bluetooth, Z-Wave, ZigBee, Wi-Fi, ANT+, near field magnetic induction (NFMI), or other applicable radio frequency signals. The personal area network may move with the user, such as between rooms in a hospital, residence, or care facility.

The wireless earpieces may include any number of sensors for measuring user biometrics, such as pulse rate, blood oxygenation, temperature, calories expended, voice and audio output, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be determined and converted into commands that may be sent to one or more external devices, such as a tablet computer, smart phone, or so forth. The user input may be particularly important for users that may not be able to coherently speak or move enough to request help or assistance (e.g., reach a nurse call button, access a cell phone, etc.).

Provider (hospitals and physician offices) data are referred to as an EMR. When the user or patient has the ability to modify the data in the electronic record without validation or prior to validation from a medical professional, the record is referred to as an electronic health record. EMRs may include clinical findings, laboratory results, radiology images, or other data. The EMRs may compiled over time or may represent a brief or limited sample of biometrics. An EMR is different than an electronic health record where the wireless earpiece user or the patient maintains the record themselves for personal use. The EMRs may represent minutes, hours, days, months, or even years of data. The user/wearer of the wireless earpieces or a medical professional may specify the data captured and integrated with the EMRs. In one embodiment, user preferences, settings, configurations, or parameters may be utilized to control how information and data is utilized to generate the EMRs.

FIG. 1 is a pictorial representation of a communication system 100 in accordance with an illustrative embodiment. In one embodiment, the communication system 100 may represent a personal area network utilized by one or more users. The communication system 100 may also represent any number of systems, environments, or networks in which a user may utilize the described devices and components. For example, an environment 101 may be representative of a hospital, care facility, nursing home, residence, office building, school, or so forth. The environment 101 may be a location wherein the user 102 spends a substantial amount of time. The environment 101 may be a monitored environment or may be a location where the user is solely present.

In one embodiment, the communication system 100 may include a user 102 utilizing wireless earpieces 104 and communicating with a communications device 106. The wireless earpieces 104 may communicate with the communications device 106 through a wireless signal 105. The wireless earpieces 104 are shown as worn and separately from their positioning within the ears of the user 102 for purposes of visualization.

In one embodiment, the wireless earpieces 104 include a frame shaped to fit substantially within the ear of the user 102. The frame is a support structure that at least partially encloses and houses the electronic components of the wireless earpieces 104. The frame may include one or more sleeves configured to fit the inside of the ear of the user 102. The sleeves may have extremely tight tolerances to fit the size and shape of the ear of the user 102. In another embodiment, the sleeves may be custom built. In some applications, temporary adhesives or securing mechanisms (e.g., clamps, straps, extenders, etc.) may be utilized to ensure that the wireless earpieces 104 remain in the ears of the user 102 even during the most rigorous and physical activities. For example, the wireless earpieces 104 may be utilized in wet or humid environments, during sports, or so forth. The wireless earpieces 104 may be configured to play music or audio, receive and make phone calls or other communications, activate and communicate with a digital assistant (e.g., Siri, Cortana, Alexa, smart assistant, etc.) determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions.

In one embodiment, the user(s) 102 is one of a group, team, or association of individuals participating in a common activity, event, game, or another happening. For example, the users 102 may represent one of a team of doctors serving in a remote location. In one embodiment, the user 102 may remove the wireless earpieces 104 and place them in the ears of a patient or individually to monitor the patient's conditions to ensure their vitals are within satisfactory ranges. The biometrics from the user 102 or a separate patient as described in the example may be utilized to generate EMR. These records may be utilized for the good of the user 102 or individual wearing the wireless earpieces 104.

In another embodiment, the user 102 may represent one individual of a team working jointly on a project, event, or operation. The user 102 may be able to communicate with one other users directly or indirectly utilizing the wireless earpieces 104. The communications system 100 may include any number of networks, repeaters, or extenders for extending the range and accessibility of the wireless earpieces 104. The communications device 106 may receive biometric information for the user 102 enabling a single person or group to monitor the status and condition of the user 102. For example, a medical professional may monitor the status, condition, and biometrics of the user. In other embodiments, the biometric data acquired for the user 102 for the corresponding wireless earpieces 104 may be sent remotely to any number of devices or systems. For example, the data may be archived in one or more remote servers and databases as an EMR for subsequent retrieval through a cloud network and interface. The EMRs may then be used for analysis, diagnosis, treatment formulation, real-time monitoring, and so forth. The information reported by the wireless earpieces 104 may be sent to a medical professional (such as a primary care physician or a specialist), emergency medical services, a designated caregiver, physical therapist, or relatives of each of the user 102, or other designated contacts. For example, a potentially dangerous impact detected by the wireless earpieces 104 for the user 102 may be reported to a caregiver utilizing the communications device 106.

The wireless earpieces 104 may be utilized for monitoring, diagnosis, early detection, and treatment of the user 102 based on an injury (e.g., head strike, hit, crash, accident, fall, etc.) or other detected health event (e.g., overheating, hypothermia, heart attack, stroke, seizure, asthma attack, electrocution, etc.). The wireless earpieces 104 may also detect a particular sound pattern or audio, such as a user groaning, screaming, or other audio event that may be associated with physical distress, a potential injury, or health event. The wireless earpieces 104 may include a library stored within their respective memories including one or more thresholds, values, user profiles, or data, for determining whether the user may be experiencing an injury or health event. The user profile may specify the age, gender, weight, height, ethnicity, health conditions, activity level, and so forth.

The devices of the communication system 100 may include any number of devices, components, or so forth that may communicate with each other directly or indirectly through a wireless (or wired) connection, signal, or link, such as the wireless signals 105. The communications system 100 may be a network and may include any number of network components and devices, such as routers, servers, signal extenders, intelligent network devices, computing devices, or so forth. The network of the communications system 100 represents a personal area network as previously disclosed. Communications, such as the wireless signals 105, within the communication system 100 may occur through the network or may occur directly between devices, such as the wireless earpieces 104 and the communications device 106 (e.g., direct communication of the wireless signal 105) or between the wireless earpieces 102 and the logging device 108 (indirect communication through a Wi-Fi network utilizing the wireless signal 105). The communications system 100 may communicate with or include a wireless network, such as a Wi-Fi, cellular (e.g., 3G, 4G, 5G, PCS, GSM, etc.), Bluetooth, or other radio frequency network. The communications system 100 may also communicate with any number of hard wired networks, such as local area networks, coaxial networks, fiber-optic networks, or so forth. Communications within the communication system 100 may be operated by one or more users, service providers, or network providers.

As noted, both the wireless earpieces 104 as well as wearable or implantable devices utilized by the user 102 may include a number of sensors including touch sensors, optical sensors, pulse oximeters, microphones, accelerometers, gyroscopes, global positioning chips, and so forth for detecting the biometrics, motion, location, and activities of the user. The information may be utilized to coordinate the audio, video, text, and graphical information presented to the user 102 (as well as the communications device 106) by the respective wireless earpieces 104. In one embodiment, the user 102 or a medical professional may program the wireless earpieces 104 to perform specific activities in response to a specific biometric reading, user motion, command or audio signal, or other action. For examples, the user 102 may configure the wireless earpieces 104 (directly or indirectly through a user interface of a computing device communicating with the wireless earpieces 104) to send a concussion alert in response to sensing forces above a specified level applied to the head of the user 102.

Any number of user and environmental conditions may be utilized to generate alerts or other communications. The alerts may also be played audibly to the user 102. For example, the user may be played an alert indicating "you may be dehydrated, consider drinking water and taking a break", or "you just experience a significant impact, are you injured?" These same informational alerts may be communicated as text or audio to the wireless device 106 and/or the logging device 108. The wireless earpieces 104 as well as the communications device 106 may include logic for automatically communicating an alert in response to events, such as the user's 102, pulse stopping or slowing significantly (e.g., code blue alert within a hospital or care facility). Thus, the communication system 100 may be adapted to the needs and desires of the user 102.

The communications device 106 may utilize short-range or long-range wireless communications to communicate with the wireless earpieces 104 through the wireless signal 105 or devices of the communications system 100 through the wireless signal 105. For example, the communications device 106 may include a Bluetooth, and cellular transceiver within the embedded logical components. For example, the wireless signal 105 may be a Bluetooth, Wi-Fi, NFMI, Zigbee, Ant+, or other short range wireless communication.

The communications device 106 may represent any number of wireless or wired electronic communications or computing devices, such as smart phones, laptops, desktop computers, control systems, tablets, displays, gaming devices, music players, personal digital assistants, vehicle systems, or so forth. The logging device 108 may represent any number of medical devices, such as heart rate monitors, electrocardiogram machines, electrosurgical units, stress systems, diagnostic ultrasounds, medical/surgical lights, sterilizers, anesthesia machines, defibrillators, patient monitors, pumps, lasers, life support equipment, diagnostic medical equipment, medical imaging, equipment, physical therapy machines, and so forth.

The communications device 106 and logging device 108 may communicate with the wireless earpieces 104 utilizing any number of wireless connections, standards, or protocols (e.g., near field communications, Bluetooth, Wi-Fi, wireless Ethernet, etc.). For example, the communications device 106 may be a touch screen cellular phone that communicates with the wireless earpieces 104 utilizing Bluetooth communications. The communications device 106 may implement and utilize any number of operating systems, kernels, instructions, or applications that may make use of the sensor data or user input received from the wireless earpieces 104. For example, the communications device 106 may represent any number of Android, iOS, Windows, open platforms, or other systems. Similarly, the communications device 106, the logging device 108, or the wireless earpieces 104 may include a number of applications that utilize the user input, biometric data, and other feedback from the wireless earpieces 104 to generate, edit, and display applicable information and data from EMRs, control the applications, play audible or tactile alerts, or make other selections. For example, biometric information (including, high, low, average, or other values) may be processed by the wireless earpieces 104, the communications device 106, or the logging device 108 to display experienced forces, heart rate, blood oxygenation, altitude, speed, distance traveled, calories burned, or other applicable information.

The wireless device 106 may include any number of input components and sensors (e.g., similar to those described with regard to the wireless earpieces 104) that may be utilized to augment the input and sensor readings of the wireless earpieces 104. For example, a microphone of the wireless device 106 may determine an amount and type of ambient noise. The noise may be analyzed and utilized to filter the sensor readings made by the wireless earpieces 104 to maximize the accuracy and relevance of the sensor measurements of the wireless earpieces 104. For example, the wireless earpieces 104 may adjust the microphone sensitivity or filter out background noise based on measurements performed by the communications device 106. Filtering, tuning, and adaptation for the sensor measurements may be made for signal noise, electronic noise, or acoustic noise, all of which are applicable in the communication system 100. Sensor measurements made by either the wireless earpieces 104 or communications device 106 may be communicated with one another in the communication system 100. As noted, the communications device 106 is representative of any number of personal computing, communications, exercise, medical, or entertainment devices that may communicate with the wireless earpieces 104.

The user 102 may also have any number of wearable or implantable medical devices that may communicate with the wireless earpieces 104, wireless device 106, or the logging device 108. In one embodiment, the range of a wearable or implantable device may be sufficient to be read by the wireless earpieces 104, but insufficient to communicate with the wireless device 106 or the logging device 108. As a result, the wireless earpieces may temporarily or permanently store information as well as relaying biometric data, inertial data, physiological data, biological data, environmental data from the wearable or implantable devices to generate and update EMRs.

The user 102 may be wearing or carrying any number of sensor-enabled devices, such as heart rate monitors, pacemakers, smart glasses, smart watches or bracelets (e.g., Apple watch, Fitbit, etc.), or other sensory devices that may be worn, attached to, or integrated with the user 102. The data and information from the external sensor devices may be communicated to the wireless earpieces 104. In another embodiment, the data and information from the external sensor devices may be utilized to perform additional processing of the information sent from the wireless earpieces 104 to the communications device 106 and/or logging device 108.

The sensors of the wireless earpieces 104 may be positioned at enantiomeric locations. For example, a number of colored light emitting diodes may be positioned to provide variable data and information, such as heart rate, respiratory rate, and so forth. The data gathered by the LED arrays may be sampled and used alone or in aggregate with other sensors. As a result, sensor readings may be enhanced and strengthened with additional data.

The wireless earpieces 104 may represent or communicate with other wireless devices that may be ingested or implanted into a user. For example, the described electronics may be endoscopic pills, pacemakers, tracking devices, contact lenses, oral implants, bone implants, artificial organs, or so forth.

Figure 2:
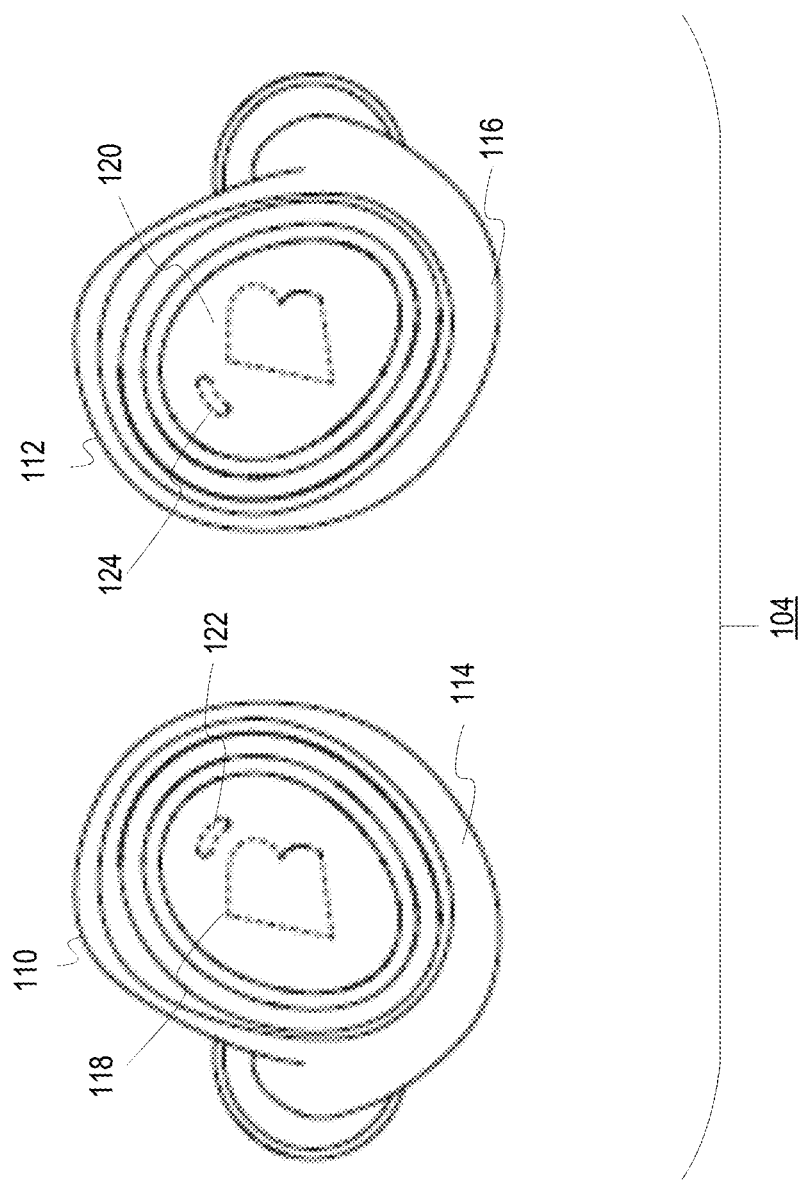
FIG. 2 is a pictorial representation of the wireless earpieces of the communications system of FIG. 1.

FIG. 2 is a pictorial representation of the wireless earpieces of the communications system of FIG. 1 in accordance with an illustrative embodiment. FIG. 2 illustrates one example of a wearable device in the form of a set of wireless earpieces 104 including a left wireless earpiece 110 and a right wireless earpiece 112. Each of the wireless earpieces 110, 112 has a housing 114, 116 which may be in the form of a protective shell, frame or casing and may be an in-the-ear earpiece housing. A left infrared through ultraviolet spectrometer 118 and right infrared through ultraviolet spectrometer 120 is also shown. Air microphones 122, 124 are also shown. Note that the air microphones 122, 124 are outward facing such that the air microphones 122, 124 may capture ambient environmental sound. It is to be understood that any number of microphones may be utilized in the illustrative embodiments.

With respect to the wireless earpieces 104, sensor measurements or user input may refer to measurements made by one or both wireless earpieces 104 in a set. For example, the right wireless earpieces 112 may determine that the user may have experienced a concussive event even though the event was not detected by the left wireless earpiece 110. The wireless earpieces 104 may also switch back and forth between sensors of the left wireless earpiece 110 and right wireless earpieces 112 in response to varying noise, errors, or more accurate signals for both of the wireless earpieces 104. As a result, the clearest sensor signal may be utilized at any given time. In one embodiment, the wireless earpieces 104 may switch sensor measurements in response to the sensor measurements exceeding or dropping below a specified threshold. In one embodiment, the wireless earpieces 104 may be split between multiple users to monitor their condition simultaneously.

Figure 3:
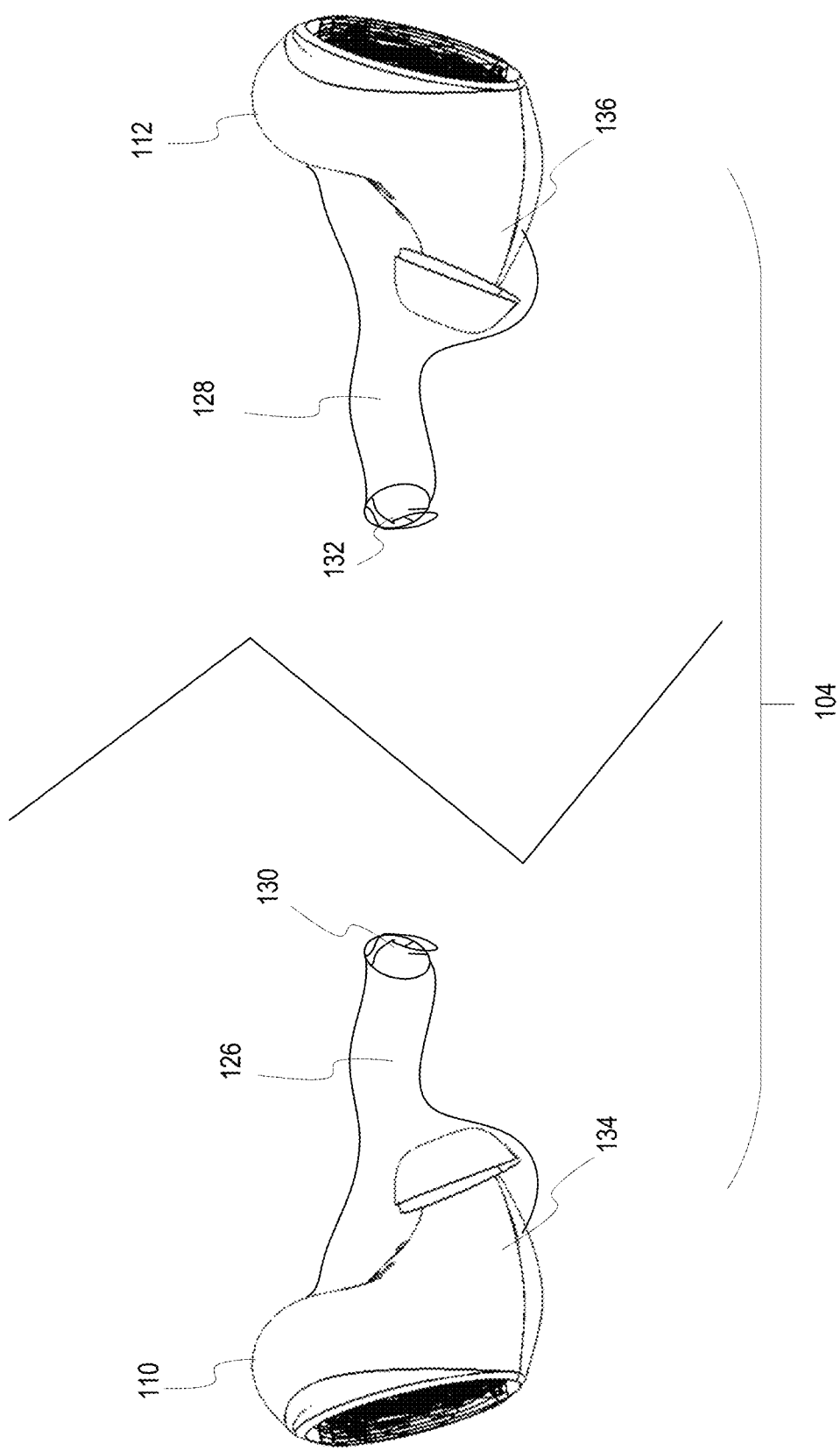
FIG. 3 illustrates a pair of wireless earpieces positioned within external auditory canals of a user.

FIG. 3 illustrates wireless earpieces 110, 112 positioned within an ear of an individual or user when worn. The wireless earpieces 110, 112 each fit at least partially into external auditory canals 126, 128 of the user. A tympanic membrane 130, 132 is shown at the end of the external auditory canal 126, 128. Note that given the placement of each earpiece 110, 112 at least partially within the external auditory canal, one or more speakers of each earpiece 110, 112 is in very close proximity to the tympanic membrane 130, 132. Given the nature of ear canal earpieces, the ability to spatially localize the sound origin within a three-dimensional environment is heightened. This allows the user to experience the programming from different points of view, or alternatively, to focus on a particular position within the three-dimensional sound sphere. Through the use of appropriate algorithms, the user is able to select a position within the sound sphere for increased immersive effect. Alternatively, instead of selecting the position within the sound sphere, the programming may drive this selection.

The wireless earpieces 110, 112 further include any number of internal microphones, such as ear-bone microphones 134, 136. The ear-bone microphones 134, 136 may represent ear-bone or bone conduction microphones. The ear-bone microphones 134, 136 may sense vibrations, waves, or sound communicated through the bones and tissue of the user's body (e.g., skull). The ear-bone microphones 134, 136 and the external microphones previously described may work together to create an accurate sound profile.

Figure 4:
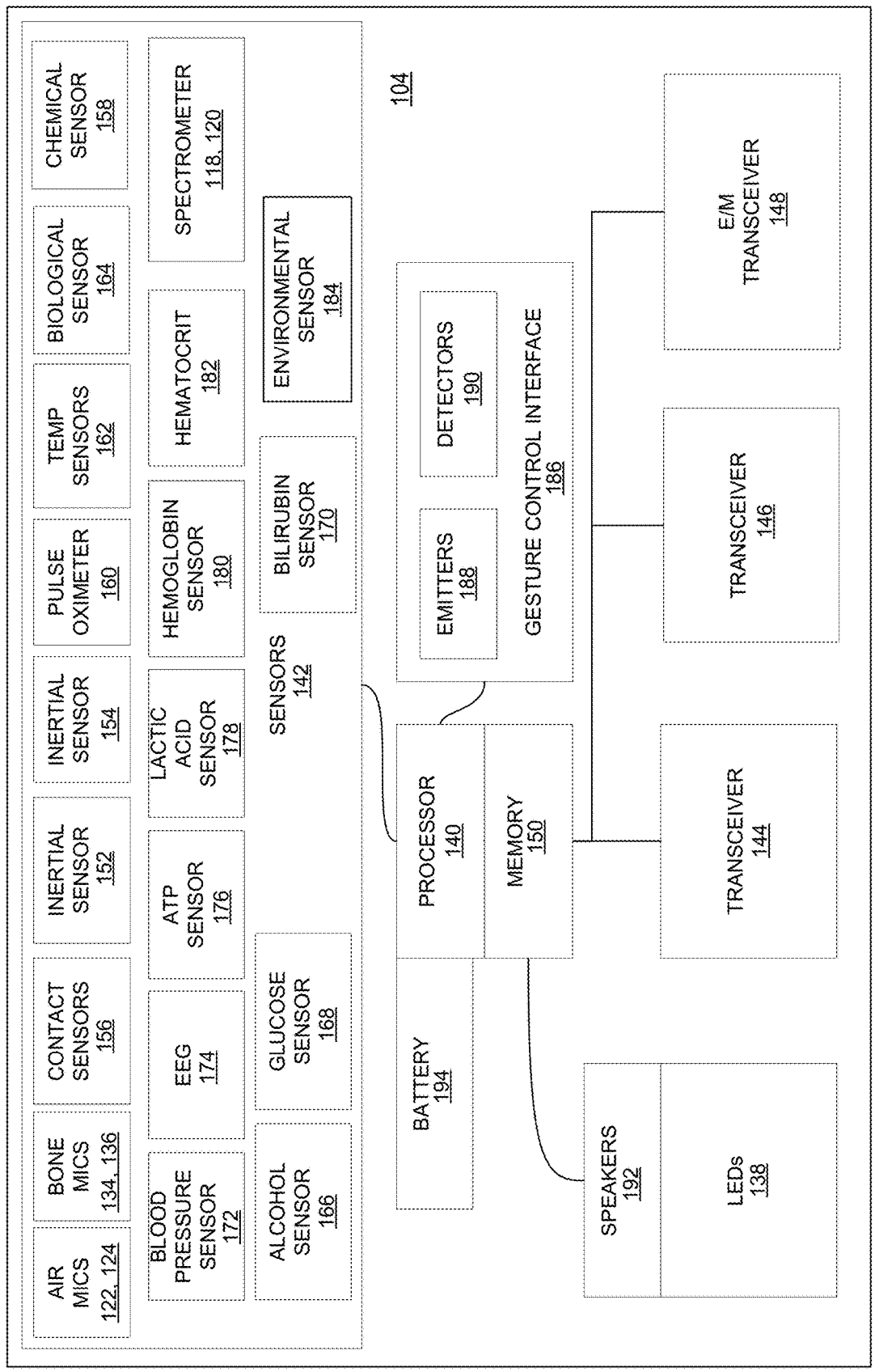
FIG. 4 is a block diagram of wireless earpieces.

FIG. 4 is a block diagram of wireless earpieces. The description of the components, structure, functions, and other elements of the wireless earpieces 104 may refer to a left wireless earpiece, a right wireless earpiece, or both wireless earpieces 104 as a set or pair. All or a portion of the components shown for the wireless earpieces 104 may be included in each of the wireless earpieces. For example, some components may be included in the left wireless earpiece, but not the right wireless earpiece and vice versa. In another example, the wireless earpieces 104 may not include all the components described herein for increased space for batteries or so forth. The wireless earpieces 104 are embodiment of wireless earpieces, such as those shown in FIGS. 1-3 (e.g., wireless earpieces 104, 110, and 112). The wireless earpieces may include one or more light emitting diodes (LEDs) 138 electrically connected to a processor 404 or other intelligent control system.

The processor 140 is the logic that controls the operation and functionality of the wireless earpieces 104. The processor 140 may include circuitry, chips, and other digital logic. The processor 140 may also include programs, scripts, and instructions that may be implemented to operate the various components of the wireless earpieces 104. The processor 140 may represent hardware, software, firmware, or any combination thereof. In one embodiment, the processor 140 may include one or more processors or logic engines. For example, the processor 140 may represent an application specific integrated circuit (ASIC) or field programmable gate array (FPGA). The processor 140 may utilize information from the sensors 142 to determine the biometric information, data, and readings of the user. The processor 140 may utilize this information and other criteria to inform the user of the biometrics (e.g., audibly, through an application of a connected device, tactilely, etc.) as well as communicate with other electronic devices wirelessly through the transceivers 144, 146, 148.

The processor 140 may also process user input to determine commands implemented by the wireless earpieces 110 or sent to the wireless earpieces 112 through the transceivers 144, 146, 148. Specific actions may be associated with biometric data thresholds. For example, the processor 140 may implement a macro allowing the user to associate biometric data as sensed by the sensors 142 with specified commands, alerts, and so forth. For example, if the temperature of the user is above or below high and low thresholds, an audible alert may be played to the user and a communication sent to an associated medical device for communication to one or more medical professionals.

A memory 150 is a hardware element, device, or recording media configured to store data or instructions for subsequent retrieval or access at a later time. The memory 150 may represent static or dynamic memory. The memory 150 may include a hard disk, random access memory, cache, removable media drive, mass storage, or configuration suitable as storage for data, instructions, and information. In one embodiment, the memory 150 and the processor 140 may be integrated. The memory may use any type of volatile or non-volatile storage techniques and mediums. The memory 150 may store information related to the status of a user, wireless earpieces 104, interconnected electronic device, and other peripherals, such as a wireless device, smart glasses, smart watch, smart case for the wireless earpieces 104, wearable device, and so forth. In one embodiment, the memory 150 may display instructions, programs, drivers, or an operating system for controlling the user interface including one or more LEDs or other light emitting components, speakers, tactile generators (e.g., vibrator), and so forth. The memory 150 may also store the thresholds, conditions, biometric data (e.g., biometric and data library) associated with biometric events, inertial data, physiological data, biological data or environmental data.

The processor 140 may also be electrically connected to one or more sensors 142. In one embodiment, the sensors 142 may include inertial sensors 152, 154 or other sensors that measure acceleration, angular rates of change, velocity, and so forth. For example, each inertial sensor 408, 410 may include an accelerometer, a gyro sensor or gyrometer, a magnetometer, a potentiometer, or other type of inertial sensor.

The sensors 142 may also include one or more contact sensors 156, one or more bone conduction microphones 122, 124, one or more air conduction microphones 134, 136, one or more chemical sensors 158, a pulse oximeter 160, a temperature sensor 162, or other physiological or biological sensors 164. Further examples of physiological or biological sensors 164 include an alcohol sensor 166, glucose sensor 168, or bilirubin sensor 170. Other examples of physiological or biological sensors 164 may also be included in the wireless earpieces 104. These may include a blood pressure sensor 172, an electroencephalogram (EEG) 174, an Adenosine Triphosphate (ATP) sensor 176, a lactic acid sensor 178, a hemoglobin sensor 180, a hematocrit sensor 182, or other biological or chemical sensor.

A spectrometer 118, 120 is also shown. The spectrometer 118, 120 may be an infrared (IR) through ultraviolet (UV) spectrometer although it is contemplated that any number of wavelengths in the infrared, visible, or ultraviolet spectrums may be detected (e.g., X-ray, gamma, millimeter waves, microwaves, radio, etc.). In one embodiment, the spectrometer 118, 120 is adapted to measure environmental wavelengths for analysis and recommendations, and thus, may be located or positioned on or at the external facing side of the wireless earpieces 104.

A gesture control interface 186 is also operatively connected to the processor 140. The gesture control interface 186 may include one or more emitters 188 and one or more detectors 190 for sensing user gestures. The emitters 188 may be of any number of types including infrared LEDs, lasers, and visible light.

The wireless earpieces may also include a number of transceivers 144, 146, 148. The transceivers 144, 146, 148 are components including both a transmitter and receiver which may be combined and share common circuitry on a single housing. The transceivers 144, 146, 148 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. The transceivers 144, 146, 148 may also be a hybrid transceiver that supports a number of different communications. For example, the transceiver 144, 146, 148 may communicate with other electronic devices or other systems utilizing wired interfaces (e.g., wires, traces, etc.), NFC or Bluetooth communications. For example, a transceiver 144 may allow for induction transmissions such as through near field magnetic induction (NFMI).

Another transceiver 146 may utilize any number of short-range communications signals, standards or protocols (e.g., Bluetooth, BLE, UWB, etc.), or other form of radio communication may also be operatively connected to the processor 140. The transceiver 146 may be utilized to communicate with any number of communications, computing, or network devices, systems, equipment, or components. The transceiver 146 may also include one or more antennas for sending and receiving signals.

In one embodiment, the transceiver 148 may be a magnetic induction electric conduction electromagnetic (E/M) transceiver or other type of electromagnetic field receiver or magnetic induction transceiver that is also operatively connected to the processor 140 to link the processor 140 to the electromagnetic field of the user. For example, the use of the transceiver 148 allows the device to link electromagnetically into a personal area network, body area network, or other device.

In operation, the processor 140 may be configured to convey different information using one or more of the LEDs 138 based on context or mode of operation of the device. The various sensors 142, the processor 140, and other electronic components may be located on the printed circuit board of the device. One or more speakers 192 may also be operatively connected to the processor 140.

The wireless earpieces 104 may include a battery 194 that powers the various components to perform the processes, steps, and functions herein described. The battery 194 is one or more power storage devices configured to power the wireless earpieces 104. In other embodiments, the battery 194 may represent a fuel cell, thermal electric generator, piezo electric charger, solar charger, ultra-capacitor, or other existing or developing power storage technologies.

Although the wireless earpieces 104 shown includes numerous different types of sensors and features, it is to be understood that each wireless earpiece need only include a basic subset of this functionality. It is further contemplated that sensed data may be used in various ways depending upon the type of data being sensed and the particular application(s) of the earpieces.

As shown, the wireless earpieces 104 may be wirelessly linked to any number of wireless or computing devices (including other wireless earpieces) utilizing the transceivers 144, 146, 148. Data, user input, feedback, and commands may be received from either the wireless earpieces 104 or the computing device for implementation on either of the devices of the wireless earpieces 104 (or other externally connected devices). As previously noted, the wireless earpieces 104 may be referred to or described herein as a pair (wireless earpieces) or singularly (wireless earpiece). The description may also refer to components and functionality of each of the wireless earpieces 104 collectively or individually.

In some embodiments, linked or interconnected devices may act as a logging tool for receiving information, data, or measurements made by the wireless earpieces 104. For example, a linked computing device may download data from the wireless earpieces 104 in real-time. As a result, the computing device may be utilized to store, display, and synchronize data for the wireless earpieces 104. For example, the computing device may display pulse rate, blood oxygenation, blood pressure, temperature, and so forth as measured by the wireless earpieces 104. In this example, the computing device may be configured to receive and display alerts that indicate a specific health event or condition has been met. For example, if the forces applied to the sensors 142 (e.g., accelerometers) indicates that the user may have experienced a concussion or serious trauma, the wireless earpieces 104 may generate and send a message to the computing device. The wireless earpieces 104 may have any number of electrical configurations, shapes, and colors and may include various circuitry, connections, and other components.

The components of the wireless earpieces 104 may be electrically connected utilizing any number of wires, contact points, leads, busses, wireless interfaces, or so forth. In addition, the wireless earpieces 104 may include any number of computing and communications components, devices or elements which may include busses, motherboards, circuits, chips, sensors, ports, interfaces, cards, converters, adapters, connections, transceivers, displays, antennas, and other similar components.

The wireless earpieces 104 may also include physical interfaces (not shown) for connecting the wireless earpieces with other electronic devices, components, or systems, such as a smart case or wireless device. The physical interfaces may include any number of contacts, pins, arms, or connectors for electrically interfacing with the contacts or other interface components of external devices or other charging or synchronization devices. For example, the physical interface may be a micro USB port. In one embodiment, the physical interface is a magnetic interface that automatically couples to contacts or an interface of the computing device. In another embodiment, the physical interface may include a wireless inductor for charging the wireless earpieces 104 without a physical connection to a charging device.

As originally packaged, the wireless earpieces 104 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 5:
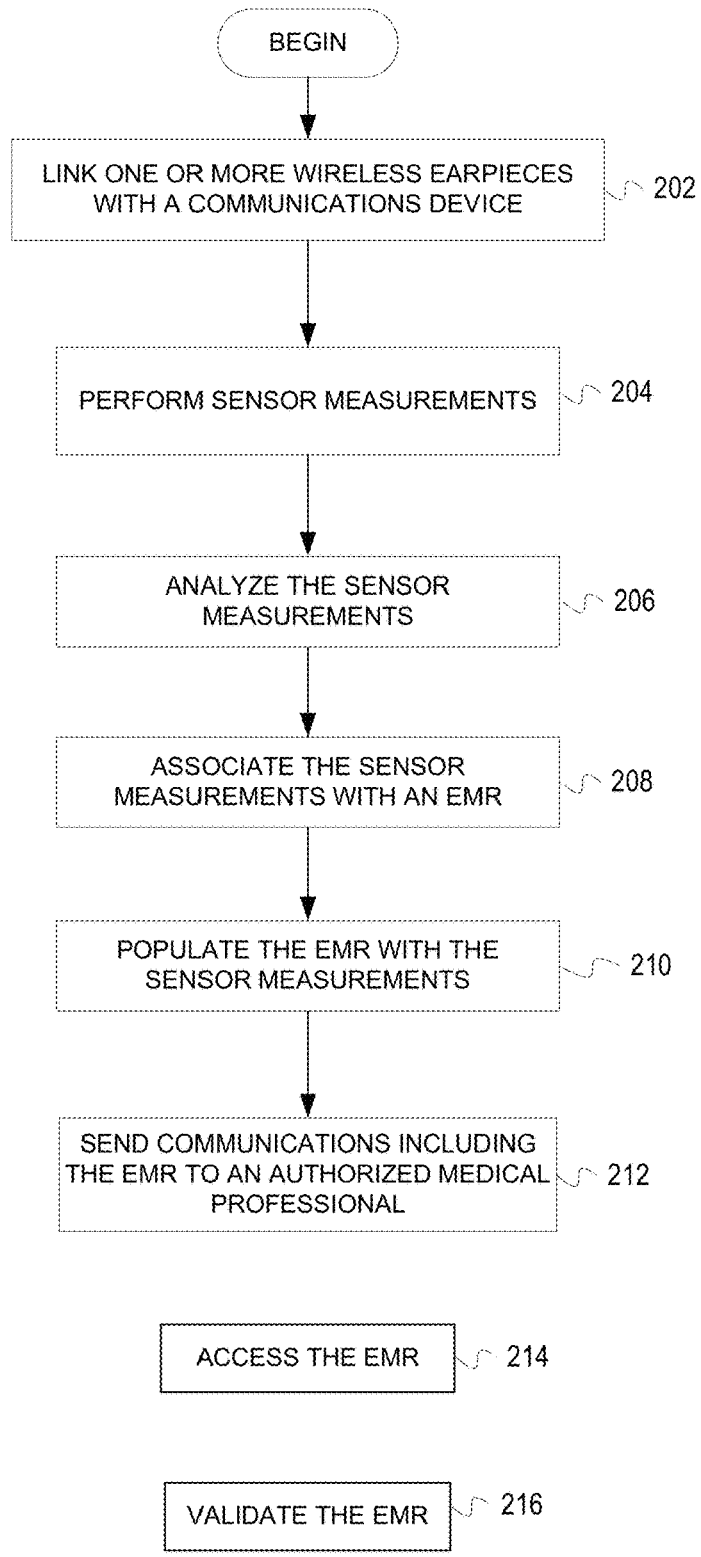
FIG. 5 is a flowchart of a process for populating electronic medical records utilizing wireless earpieces.

FIG. 5 is a flowchart of a process for populating EMRs utilizing wireless earpieces and then sending the EMR to a medical professional for validation. The process of FIG. 5 may be implemented by one or more wireless earpieces. The wireless earpieces may be in communication wearable devices, medical implants, monitors, and/or any number of communication or computing devices referred to in FIG. 5 as a communication device for purposes of simplicity. The method of FIG. 5 may be performed by a set of wireless earpieces for each of the wireless earpieces individually. The wireless earpieces may also communicate directly or indirectly with the communication device through a personal area network or other network. The process of FIG. 5 may be performed utilizing logic of the wireless earpieces including hardware, software, firmware, or a combination thereof. In one embodiment, an application may be utilized to generate and populate an EMR based on sensor measurements associated with a user. In one embodiment, wireless earpieces with different sensor arrays may be utilized by different users, providers, and for differing circumstances of the user. As a result, the read sensor measurements may vary for personal use, nursing homes, athletic facilities, hospitals, office workspaces, triage centers, and so forth.

The process of FIG. 5 may begin by linking one or more wireless earpieces with a communications device (step 202). The wireless earpieces may be linked with the communications device utilizing any number of communications, standards, or protocols. For example, the devices may be linked by a Bluetooth connection. The process may require that the devices be paired utilizing an identifier, such as a passcode, password, serial number, voice identifier, radio frequency, or so forth. The wireless earpieces may be linked with the communications device and any number of other devices directly or through a network, such as a personal area network. The wireless earpieces and the communication device may be linked, connected, or paired, such that any time they are within range or approximate each other, they may begin communicating.

Next, the wireless earpieces perform sensor measurements (step 204). The sensor measurements may include performing any number of biometric, inertial, physiological, biological, and environmental measurements applicable to the user. The measurements may be performed utilizing a predefined sampling rate (e.g., 1 second, 100 milliseconds, once a minute, etc.). The sensor measurements may also be triggered in response to detected events or thresholds, such as change in user orientation or position (e.g., change from vertical to horizontal position), changes in velocity (e.g., extreme starts, stops, accelerations, etc.), high forces (e.g., impacts, jolts, etc.), or detected events from other sensors worn by the user. The sensor measurements may also be performed in response to any number of settings, instructions, requests, feedback, programs, or so forth. The settings may be specified by the user, a medical professional, a health monitoring program, a guardian, or other authorized user. For example, a medical professional associated with the user may utilize a graphical user interface available through the communication's device (or other associated device) to set the times, conditions, events, circumstances, stimuli, biometrics, location, user orientation or other factors utilized to perform the sensor measurements. The sensor measurements may be performed specifically to generate or update an associated EMR.

Next, the wireless earpieces analyze the sensor measurements (step 206). The sensor measurements may be processed or otherwise evaluated by the wireless earpieces. For example, one or more processors of the wireless earpieces may process the incoming sensor data measurements. For example, the analysis may include determining or verifying one of a potential number of users utilizing the wireless earpieces. To further illustrate, an EMR may only be generated and updated for a child previously associated with the wireless earpieces (e.g., a user profile has been established). The analysis may also include processing raw data from the wireless earpieces to generate values, data, or other input that may be integrated with the EMR. This information may be a summary of the sensor measurements or a compilation of the sensor measurements. This may include specifically identifying high values, low values, averages, ranges for readings, durations within particular ranges, and other information. The sensor measurements are processed for subsequent analysis, determinations, or decisions, implemented by the wireless earpieces.

Next, the wireless earpieces associate the sensor measurements with an EMR (step 208). The sensor measurements of step 208 may represent the analyzed or processed measurements as performed during step 206 (e.g., values, data points, information, etc.). In one embodiment, the wireless earpieces may associate the identified user with an associated EMR. Any number of names, identifiers, profiles or other information included in or integrated with the wireless earpieces or the EMR may be utilized to ensure that the sensor measurements are associated with the corresponding EMR.

Next, the wireless earpieces populate the EMR with the sensor measurements (step 210). The EMR may be populated or updated utilizing real-time measurements, at specified intervals, utilizing queued/saved data, or so forth. In one embodiment, an EMR may be generated for the user. For example, during any of the steps of FIG. 5, an EMR may be created for a specified user. A template, form, database, web/cloud interface, or other specified information may be utilized to create the blank EMR for the user. In another embodiment, the EMR may already exist for the user, and thus, the EMR may be further populated with data during step 210. For example, heart rate, temperature, blood pressure, and motion of the user may be associated with particular fields, parameters, or settings and may specify a date/time of the sensor measurements. Additional data may also be associated with the EMR, such as position, orientation, location, additional users proximate or in communication with the user, and other applicable information. In one embodiment, the EMR may be populated as an automated process. In another embodiment, the EMR may be updated in response to one or more biometric thresholds associated with the user being exceeded. The wireless earpieces may populate all of the EMR or only data fields or portions of the EMR associated with the sensor measurements.

The wireless earpieces may populate the EMR with identifying information for a user. This may include patient identifiers associated with an individual, date of birth, social security number, and other information commonly used to identify a patient within an EMR for the patient. The wireless earpieces may also populate the EMR with information about the wireless earpieces used to collect the data. This may include manufacturer, model, serial number, functionality, or other information.

Next, the wireless earpieces send communications including the EMR to at least the communications device (step 212) associated with the authorized medical profession for validation. The wireless earpieces may send the EMR to any number of specified or default users, devices, systems, equipment, components, or so forth. For example, the EMR may be communicated to a wireless device, such as a smart phone. The smart phone may then relay the EMR to a server, monitoring system, web/cloud interface, or so forth. As a result, the medical professional associated with the user may be able to view the most recent data, information, values, and updates of the EMR as associated biometric data is captured by the wireless earpieces. In another example, the EMR may be sent directly to a tablet of a doctor. The EMR may be displayed utilizing an application that presents the EMR visually (e.g., graphs, charts, thresholds, trends, averages, data points, etc.), mathematically, audibly, or so forth. The information shared by the wireless earpieces 104 is approved by the user or a guardian of the user.

Next, the authorized medical professional accesses the updated or newly generated EMR (Step 214). The medical professional may access the EMR using various techniques such as a password, a personal identity number, a unique web address associated with the user's EMR, security questions and so forth. The EMR includes a consent document giving permission for the medical professional to view the EMR.

Next, the authorized medical professional validates the updated or newly generated EMR (Step 216). Internal validation processes are performed using various techniques, which may include probability assessment by the medical professional, referential edits, algorithms and/or other techniques to determine that data elements of the updated or newly generated EMR are correct before adding the data permanently to the EMR. In another embodiment the medical professional may use unique identifiers to validate that the user the wireless earpieces associated with the EMR is correct. The medical professional may use biometric data such as heart rate, blood pressure, the EEG sensor and so forth. The validation of step 216 may involve receiving confirmation of validation by the medical professional or other health care provider and storing the validation or approval of the health care provider of the biometric data into the EMR.

Figure 6:
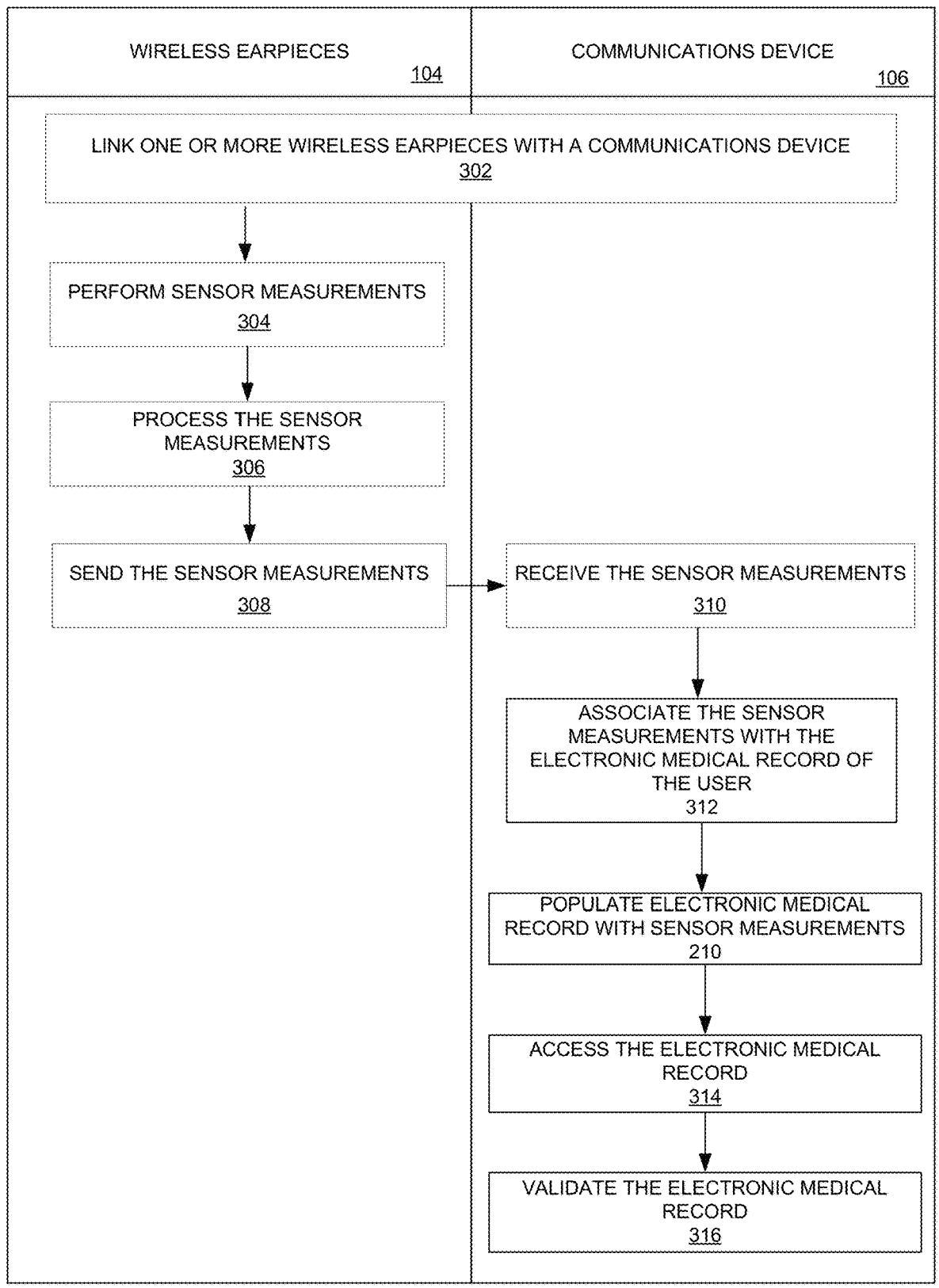
FIG. 6 is a flowchart of a process for populating electronic medical records between devices utilizing wireless earpieces.

FIG. 6 is a flowchart of a process for populating electronic medical records between devices utilizing wireless earpieces in accordance with an illustrative embodiment. The process of FIG. 6 may be implemented by wireless earpieces 104 and a communications device 106. Many of the steps and description with regard to FIG. 5 are similarly applicable to FIG. 6.

In one embodiment, the process may begin by linking the wireless earpieces 104 with the communications device 106 (step 302). As previously noted, any number of standards, protocols, or signals may be utilized to connect, associate, or link the wireless earpieces 104 with the communications device 106.

Next, the wireless earpieces 104 perform sensor measurements (step 304). In addition, to the wireless earpieces 104, sensor measurements may be taken by the communications device 604, implantable devices, wearable devices (e.g., smart or biometric watches, wristbands, headbands, jewelry, etc.).

Next, the wireless earpieces 104 process the sensor measurements (step 306). During step 306, the wireless earpieces 104 may process the raw data into a format that may be utilized by the communications device 106. For example, the wireless earpieces 104 may convert the raw data into data, values, or information that may be more easily inserted into the EMR. In one example, the processing may include associating a time stamp with the biometrics read by the wireless earpieces 104. As a result, a medical professional reading the EMR may have a time and date associated with biometric data of interest. In other embodiments, the wireless earpieces 104 may further associated information, such as location, orientation, position, user detected activity, user voice output (e.g., speech recordings, voice-to-text translations, stress levels, amplitude, frequency, etc.). The information shared by the wireless earpieces 104 is approved by the user or a guardian of the user. The wireless earpieces 104 may also process the sensor measurements into a format that is more easily communicated to the communications device 104 which may include packetization, frame generation, signal processing and preparation, data encryption, digital-to-analog conversion, data compression, modulation, coding, and so forth.

Next, the wireless earpieces 104 send the sensor measurements to the communications device 106 (step 308). The sensor measurements may be communicated to the communication device 106 as well as any number of other devices, simultaneously, sequentially, concurrently, or so forth.

Next, the communications device 106 receive the sensor measurements (step 310). An established link, connection, or signals may be utilized to communicate the sensor measurements during step 310. In one embodiment, the communications are performed directly utilizing a signal, such as Bluetooth, Wi-Fi, or so forth.

Next, communications device 106 associates the sensor measurements with an electronic medical record (step 312). In one embodiment, the wireless earpieces 104 may have been associated with a particular user. For example, device identifiers for the wireless earpieces 104 may be associated with an electronic medical record to ensure that information is properly recorded, authenticated, stored, and subsequently accessed. In one embodiment, user biometrics (e.g., voice authentication, skin conductivity, fingerprint analysis, etc.) may be utilized by the wireless earpieces 104 to associate the user with the wireless earpieces 104 and the sensor measurements with an associated electronic medical record.

Next, the medical professional accesses the EMR on the communication device 106 (step 314). The medical professional may access the EMR using various techniques such as a password, a personal identity number, a unique web address associated with the user's EMR, security questions and so forth. The EMR includes a consent document giving permission for the medical professional to view the EMR. As a result, the medical professional associated with the user may be able to view the most recent data, information, values, and updates of the EMR as associated biometric data is captured by the wireless earpieces. The EMR may be displayed utilizing an application that presents the EMR visually (e.g., graphs, charts, thresholds, trends, averages, data points, etc.), mathematically, audibly, or so forth.

Next, the authorized medical professional validates the updated or newly generated EMR (Step 316). Internal validation processes are performed using various techniques, which may include probability assessment by the medical professional, referential edits, algorithms and/or other techniques to determine that data elements of the updated or newly generated EMR are correct before adding the data permanently to the EMR. In another embodiment the medical professional may use unique identifiers to validate that the user the wireless earpieces associated with the EMR is correct. The medical professional may use biometric data such as heart rate, blood pressure, the EEG sensor and so forth. A record of the validation of approval of the biometric data as a part of the medical record may be stored within the electronic medical record.

Figure 7:
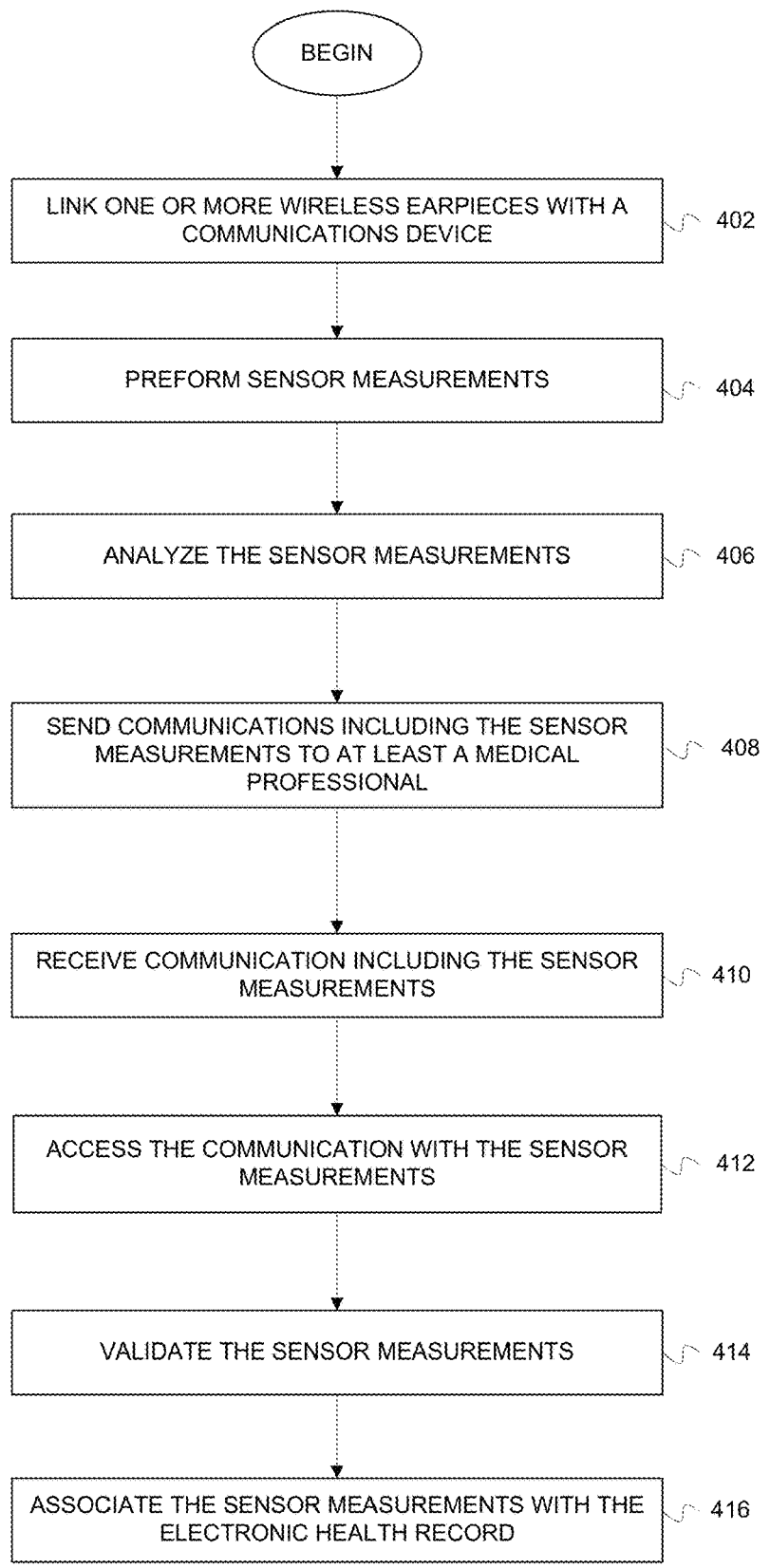
FIG. 7 depicts a method for populating an electronic medical record.

FIG. 7 is a flowchart of a process for populating electronic medical records utilizing the sensor measurements from the wireless earpiece. Many of the steps and description with regard to FIG. 5 and FIG. 6 are similarly applicable to FIG. 7.

In one embodiment, the process may begin by linking the wireless earpieces 104 with the communications device 106 (step 402). As previously noted, any number of standards, protocols, or signals may be utilized to connect, associate, or link the wireless earpieces 104 with the communications device 106.

Next, the wireless earpieces 104 perform sensor measurements (step 404). In addition, to the wireless earpieces 104, sensor measurements may be taken by the communications device 604, implantable devices, wearable devices (e.g., smart or biometric watches, wristbands, headbands, jewelry, etc.).

Next, the wireless earpieces 104 analyze the sensor measurements (step 406). During step 306, the wireless earpieces 104 may process the raw data into a format that may be utilized by the communications device 106. For example, the wireless earpieces 104 may convert the raw data into data, values, or information that may be more easily inserted into the EMR. In one example, the processing may include associating a time stamp with the biometrics read by the wireless earpieces 104. As a result, a medical professional reading the EMR may have a time and date associated with biometric data of interest. In other embodiments, the wireless earpieces 104 may further associated information, such as location, orientation, position, user detected activity, user voice output (e.g., speech recordings, voice-to-text translations, stress levels, amplitude, frequency, etc.). The information shared by the wireless earpieces 104 is approved by the user or a guardian of the user. The wireless earpieces 104 may also process the sensor measurements into a format that is more easily communicated to the communications device 104 which may include packetization, frame generation, signal processing and preparation, data encryption, digital-to-analog conversion, data compression, modulation, coding, and so forth.

Next, the wireless earpieces 104 send the sensor measurements to the communications device 106 (step 408). The sensor measurements may be communicated to the communication device 106 as well as any number of other devices, simultaneously, sequentially, concurrently, or so forth.

Next, the communications device 106 associated with a medical professional receive the sensor measurements (step 410). An established link, connection, or signals may be utilized to communicate the sensor measurements during step 410. In one embodiment, the communications are performed directly utilizing a signal, such as Bluetooth, Wi-Fi, or so forth. As a result, the medical professional associated with the user may be able to view the most recent data, information, values, and updates of the EMR as associated biometric data is captured by the wireless earpieces.

Next, the medical professional accesses the sensor measurements on the communication device 106 (step 412). The medical professional may access the sensor measurements using various techniques such as a password, a personal identity number, a unique web address associated with the user's sensor measurements, security questions and so forth.

Next, the authorized medical professional validates the sensor measurements (Step 414). Internal validation processes are performed using various techniques, which may include probability assessment by the medical professional, referential edits, algorithms and/or other techniques to determine that data elements of the sensor measurements are correct before adding the data permanently to the EMR. In another embodiment the medical professional may use unique identifiers to validate that the user the wireless earpieces associated with the sensor measurements is correct. The medical professional may use biometric data such as heart rate, blood pressure, the EEG sensor and so forth.

Next, medical professional associates the sensor measurements with an electronic medical record (step 416). In one embodiment, the wireless earpieces 104 may have been associated with a particular user. For example, device identifiers for the wireless earpieces 104 may be associated with an electronic medical record to ensure that information is properly recorded, authenticated, stored, and subsequently accessed. In one embodiment, user biometrics (e.g., voice authentication, skin conductivity, fingerprint analysis, etc.) may be utilized by the wireless earpieces 104 to associate the user with the wireless earpieces 104 and the sensor measurements with an associated electronic medical record. The EMR may be displayed utilizing an application that presents the EMR visually (e.g., graphs, charts, thresholds, trends, averages, data points, etc.), mathematically, audibly, or so forth.

In additional embodiments and steps, the wireless earpieces or the communications device 106 may determine whether sensor measurement thresholds are exceeded. The wireless earpieces may include any number of thresholds, including, high and low thresholds for measurements, such as forces experienced by the user, acceleration, temperature, pulse rate, blood oxygenation, blood pressure, and so forth.

In response to determining the sensor measurement thresholds are exceeded, the wireless earpieces may send communications regarding the user's condition to the communications device for recording in the electronic medical record. For example, the communications may be an alert, status update, warning, or other similar information. In one embodiment, the communication may be an alert indicating that the user may have experienced a concussion. Likewise, the communication may indicate that the user's temperature has exceeded a threshold and may be experiencing overheating. The information from the wireless earpieces may be particularly valuable for users, such as patients in a hospital that need close monitoring. For example, the wireless earpieces may be utilized to ensure that a patient's temperature does not spike based on an experienced sickness. The communications device 106 may be monitored by medical professionals, guardians, health services groups, parents, or other monitoring groups to ensure the safety of the user. Additional sensors may be utilized as needed to monitor the user and verify measurements before one or more actions are performed. For example, additional measurements may be taken by a smart watch, or chest strap worn by the user. In another example, a pacemaker of the user may provide additional data regarding pulse, heart rhythm, and other applicable or measured information.

The illustrative embodiments provide a system, method, personal area network, and wireless earpieces for communicating sensor measurements to one or more externally connected devices. The sensor measurements are utilized to update electronic medical records, send communications, updates, alerts, or other information relative to the condition of the user as well as the user's environment. In one embodiment, the sensor measurements may be utilized to monitor, protect, diagnose, and treat the user based on one or more sensor measurements that are made, such as potential head trauma, overheating, dropping body temperature, low blood oxygenation, excessive or low heart rate, high or low blood pressure, or other applicable information determined by the sensors of the wireless earpieces.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 8:
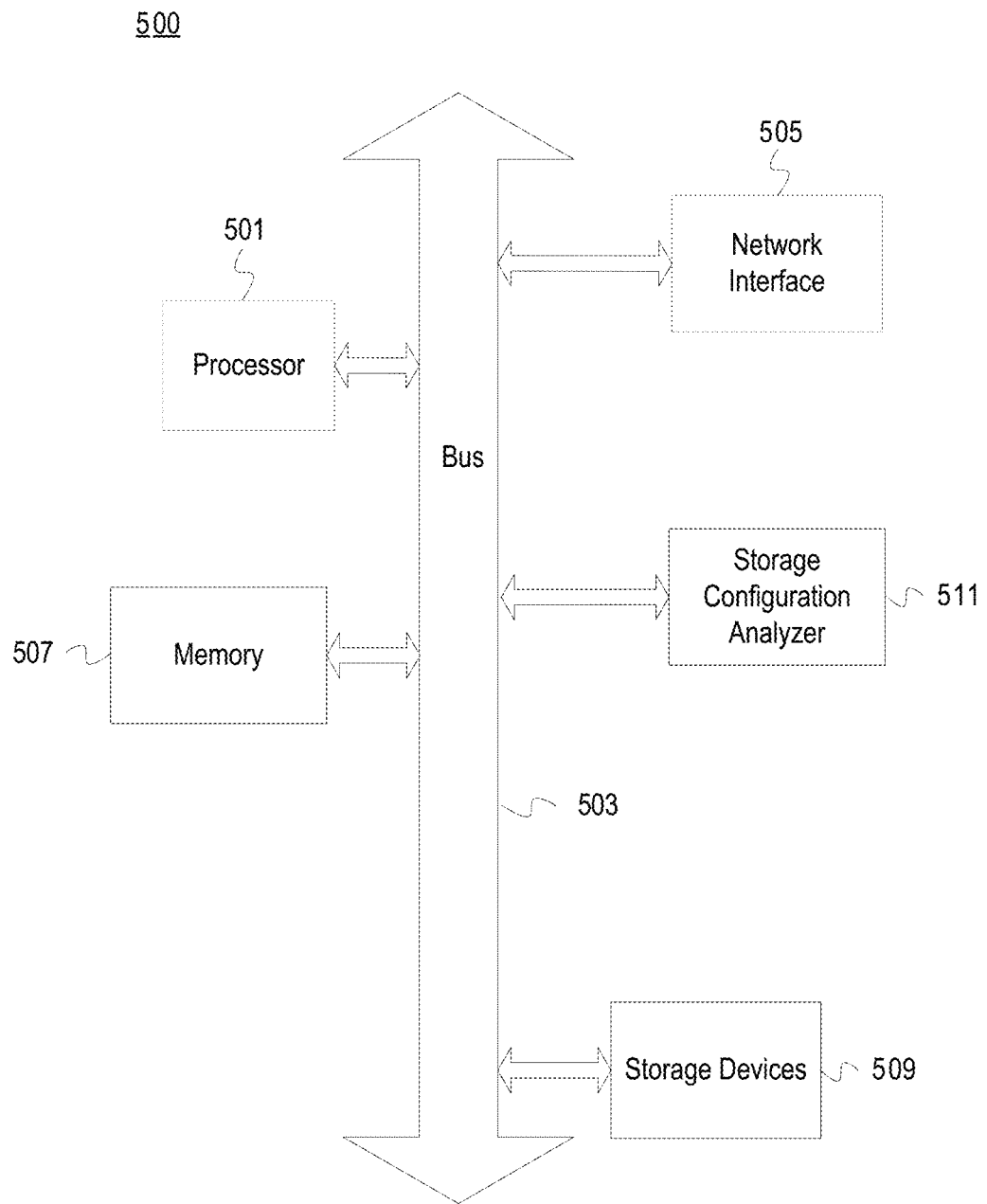
FIG. 8 depicts a computing system.

FIG. 8 depicts a computing system 500 in accordance with an illustrative embodiment. For example, the computing system 500 may represent a device, such as the wireless device 106 or the logging device 108 of FIG. 1. The computing system 500 includes a processor unit 501 (possibly including multiple processors, multiple cores, multiple nodes, and/or implementing multi-threading, etc.). The computing system includes memory 507. The memory 507 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 503 (e.g., PCI, ISA, PCI-Express, HyperTransport®, Infini-Band®, NuBus, etc.), a network interface 505 (e.g., an ATM interface, an Ethernet interface, a Frame Relay interface, SONET interface, wireless interface, etc.), and a storage device(s) 509 (e.g., optical storage, magnetic storage, etc.). The system memory 507 embodies functionality to implement embodiments described above. The system memory 507 may include one or more functionalities that facilitate creating, updating, and accessing EMRs based on communications with one or more wireless earpieces. Code may be implemented in any of the other devices of the computing system 500. Any one of these functionalities may be partially (or entirely) implemented in hardware and/or on the processing unit 501. For example, the functionality may be implemented with an application specific integrated circuit, in logic implemented in the processing unit 501, in a co-processor on a peripheral device or card, etc. Further, realizations may include fewer or additional components not illustrated in FIG. 8 (e.g., video cards, audio cards, additional network interfaces, peripheral devices, etc.). The processor unit 501, the storage device(s) 509, the storage configuration analyzer 511, and the network interface 505 are coupled to the bus 503. Although illustrated as being coupled to the bus 503, the memory 507 may be coupled to the processor unit 501.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure.

The previous detailed description is of a small number of embodiments for implementing the invention and is not intended to be limiting in scope. The following claims set forth a number of the embodiments of the invention disclosed with greater particularity.

What is claimed is:

1. A method for populating an electronic medical record (EMR), comprising:

provinding wireless earpieces wherein the wireless earpieces comprise at least one earpiece further comprising: a frame, at least one microphone, a processor operatively connected to the at least one microphone, a wireless transceiver for connecting to the wireless device, the wireless transceiver operatively connected to the processor, at least one biometric sensor operatively connected to the processor, at least one inertial sensor operatively connected to the processor, and at least one memory operatively connected to the processor and disposed within the frame;

determining by the wireless earpieces an identity of a user of the wireless earpieces;

linking the wireless earpieces to a wireless device associated with a health care provider;

receiving at the wireless earpieces and from the wireless device associated with the health care provider a plurality of EMR settings used for performing a set of sensor measurements of the user of the wireless earpieces;

performing the set of sensor measurements of the user of the wireless earpieces utilizing the at least one biometric sensor, the at least one microphone and the at least one inertial sensor of the wireless earpieces based on the EMR settings received from the health care provider;

wherein the set of sensor measurements comprises at least position data of the user and orientation data of the user sensed by the at least one inertial sensor and biometric data of the user sensed by the at least one biometric sensor;

wherein the set of sensor measurements further comprises a date and time associated with the set of sensor measurements;

determining by the wireless earpieces that the EMR is associated with the identity of the user of the wireless earpieces;

populating the EMR of the user of the wireless earpieces with the set of sensor measurements and the associated date and time of the set of sensor measurements, the populating performed by the processor of the wireless earpiece;

populating the EMR of the user with information about the wireless earpieces, the populating performed by the processor, wherein the information comprises at least an identifier of the wireless earpieces;

storing the populated EMR of the user of the wireless earpieces in the memory of the wireless earpieces;

sending communications including the populated EMR of the user with the set of sensor measurements from the wireless earpieces to the wireless device associated with the health care provider;

receiving validation of the set of sensor measurements of the populated EMR of the user of the wireless earpieces at the processor of the wireless earpieces from the health care provider utilizing the wireless device; and storing a record of the validation within the EMR in the memory of the wireless earpieces.

2. The method of claim 1 further comprising generating the EMR of the user at the wireless earpieces wherein the EMR comprises a plurality of fields and wherein a first field of the plurality of fields is associated with the biometric data and a second field of the plurality of fields is associated with the model of the wireless earpieces.

3. The method of claim 2 further comprising populating the EMR with patient identifying information in a third field of a plurality of fields of the EMR, the populating the EMR with patient identifying information performed by the processor of the wireless earpieces.

4. The method of claim 1, wherein the biometric data include at least pulse, blood pressure, temperature, and user experienced forces.

5. The method of claim 1, wherein the biometric data includes pulse data.

6. The method of claim 1, wherein the biometric data includes blood pressure data.

7. The method of claim 1 wherein the biometric data includes temperature data.

8. The method of claim 1 wherein the biometric data includes user experienced force data.

9. The method of claim 1 wherein the identifier comprises a model of the wireless earpieces.

10. A wireless earpiece, comprising:

a frame for fitting in an ear of a user;

a processor controlling functionality of the wireless earpiece;

a plurality of sensors including at least one biometric sensor, at least one microphone, and at least one inertial sensor to perform sensor measurements of the user;

a transceiver communicating with at least a wireless device;

a speaker;

a memory;

wherein the wireless earpiece is configured to:

determine an identity of the user, link the wireless earpiece to a wireless device associated with a health care provider, receive from the wireless device associated with the health care provider a plurality of EMR settings used for performing a set of sensor measurements of the user, perform the set of sensor measurements of the user utilizing the at least one biometric sensor, the at least one microphone and the at least one inertial sensor based on the EMR settings received from the health care provider, wherein the set of sensor measurements comprises at least position data of the user and orientation data of the user sensed by the at least one inertial sensor and biometric data of the user sensed by the at least one biometric sensor, wherein the set of sensor measurements further comprises a date and time associated with the set of sensor measurements;

determine that the EMR is associated with the identity of the user of the wireless earpiece;

populate the EMR of the user with the set of sensor measurements and the associated date and time of the set of sensor measurements;

populate the EMR of the user with information about the wireless earpiece, the populating performed by the processor, wherein the information comprises at least an identifier for the wireless earpiece;

store the populated EMR of the user in the memory of the wireless earpiece;

send communications including the populated EMR of the user with the set of sensor measurements from the wireless earpiece to the wireless device associated with the health care provider;

receive validation of the set of sensor measurements of the populated EMR of the user from the health care provider utilizing the wireless device; and store a record of the validation within the EMR in the memory of the wireless earpiece.

11. The wireless earpiece of claim 10, wherein the transceiver establishes a Bluetooth link with the wireless device.

12. The wireless earpiece of claim 11, wherein the EMR of the user is populated with the set of sensor measurements in response to the sensor measurements exceeding a threshold associated with the user.

13. The wireless earpiece of claim 12, wherein the sensor measurements further include at least pulse, blood pressure, audio, blood oxygenation, and temperature.

14. The wireless earpiece of claim 12 wherein the sensor measurements include pulse measurements.

15. The wireless earpiece of claim 12 wherein the sensor measurements include blood pressure measurements.

16. The wireless earpiece of claim 12 wherein the sensor measurements include temperature measurements.

17. A method for populating an electronic medical record (EMR), comprising:

providing wireless earpieces wherein the wireless earpieces comprise at least one earpiece further comprising: a frame, at least one microphone, a processor operatively connected to the at least one microphone, a wireless transceiver for connecting to the wireless device, the wireless transceiver operatively connected to the processor, at least one biometric sensor operatively connected to the processor, at least one inertial sensor operatively connected to the processor, and at least one memory operatively connected to the processor and disposed within the frame;

determining by the wireless earpieces an identity of a user of the wireless earpieces;

linking the wireless earpieces to a wireless device associated with a health care provider, wherein the wireless earpieces;

receiving at the wireless earpieces and from the wireless device associated with the health care provider a plurality of EMR settings used for performing a set of sensor measurements of the user of the wireless earpieces;

performing the set of sensor measurements of the user of the wireless earpieces utilizing the at least one biometric sensor, the at least one microphone and the at least one inertial sensor of the wireless earpieces based on the EMR settings received from the health care provider;

wherein the set of sensor measurements comprises at least position data of the user and orientation data of the user sensed by the at least one inertial sensor and biometric data of the user sensed by the at least one biometric sensor;

determining by the wireless earpieces that the EMR is associated with the identity of the user of the wireless earpieces;

populating the EMR of the user of the wireless earpieces with the set of sensor measurements and the associated date and time of the set of sensor measurements, the populating performed by the processor of the wireless earpiece;

populating the EMR of the user with information about the wireless earpieces, the populating performed by the processor;

storing the populated EMR of the user of the wireless earpieces in the memory of the wireless earpieces;

sending communications including the populated EMR of the user with the set of sensor measurements from the wireless earpieces to the wireless device associated with the health care provider;

receiving validation of the set of sensor measurements of the populated EMR of the user of the wireless earpieces at the processor of the wireless earpieces from the health care provider utilizing the wireless device; and storing a record of the validation within the EMR in the memory of the wireless earpieces.

18. The method of claim 17 further comprising generating the EMR of the user at the wireless earpieces wherein the EMR comprises a plurality of fields and wherein a first field of the plurality of fields is associated with the biometric data and a second field of the plurality of fields is associated with the model of the wireless earpieces.

19. The method of claim 18 further comprising populating the EMR with patient identifying information in a third field of a plurality of fields of the EMR, the populating the EMR with patient identifying information performed by the processor of the wireless earpieces.

20. The method of claim 17, wherein the biometric data include at least pulse, blood pressure, temperature, and user experienced forces.

* * * * *